United States Patent [19]

Louderback

[11] 4,325,832

[45] Apr. 20, 1982

[54] ENZYME REFERENCE COMPOSITION

[75] Inventor: Allan L. Louderback, Temple City, Calif.

[73] Assignee: Beckman Instruments, Inc., Fullerton, Calif.

[21] Appl. No.: 114,009

[22] Filed: Jan. 21, 1980

Related U.S. Application Data

[63] Continuation-in-part of Ser. No. 17,871, Mar. 5, 1979, abandoned.

[51] Int. Cl.³ .................. G01N 33/16; C09K 3/00
[52] U.S. Cl. .................. 252/408; 23/230 B; 424/2; 424/3; 435/2; 435/4; 435/15; 435/16; 435/17; 435/18; 435/19; 435/20; 435/21; 435/22; 435/24; 435/25; 435/26; 435/188
[58] Field of Search .............. 252/408; 23/230 B; 435/2, 4, 21, 18, 22, 20, 17, 24, 26, 15, 16, 19, 25, 188; 424/2, 3

[56] References Cited

U.S. PATENT DOCUMENTS

| | | | |
|---|---|---|---|
| 3,466,249 | 9/1969 | Anderson | 252/408 |
| 3,558,522 | 1/1971 | Louderback et al. | 252/408 |
| 3,629,142 | 12/1971 | Marbach | 252/408 |
| 3,682,835 | 8/1972 | Louderback | 252/408 |
| 3,728,226 | 4/1973 | Louderback | 252/408 |
| 3,853,465 | 12/1974 | Rush et al. | 252/408 |
| 3,876,375 | 4/1975 | Maurukas | 252/408 |
| 4,007,008 | 2/1977 | Becker et al. | 252/408 |
| 4,121,905 | 10/1978 | Maurukas | 252/408 |
| 4,141,856 | 2/1979 | Dorwart, Jr. et al. | 252/408 |
| 4,158,544 | 6/1979 | Louderback | 252/408 |
| 4,212,939 | 7/1980 | Myrick et al. | 252/408 |

OTHER PUBLICATIONS

Tietz, *Fundamentals of Clinical Chemistry*, W. B. Saunders Co., Philadelphia, Pa., p. 634, (1970).
Henry et al., Clinical Chemistry, Principles and Technics, 2nd Ed., Harper & Rowe, New York, N. Y., pp. 774–778, (1974).

*Primary Examiner*—Teddy S. Gron
*Attorney, Agent, or Firm*—R. J. Steinmeyer; J. E. Vanderburgh; Robert S. Frieman

[57] ABSTRACT

A stable enzyme reference composition having an excellent shelf-life. The composition comprises at least one enzyme of known value; about 20 to about 40 weight percent of at least one alkylene polyol having from 2 to 5 carbon atoms; about 3 to about 8 grams (gm) per deciliter (dl) total protein present in a human serum albumin matrix; and about 60 to about 80 weight percent water.

12 Claims, No Drawings

ENZYME REFERENCE COMPOSITION

CROSS REFERENCES TO RELATED APPLICATION

This application is a continuation-in-part of application Ser. No. 17,871, filed Mar. 5, 1979, now abandoned.

BACKGROUND OF THE INVENTION

1. Field of the Invention

This invention relates to a laboratory material and, more particularly, to a stable enzyme reference composition.

2. Description of the Prior Art

Various compositions capable of being employed in conjunction with the analysis of enzymes, to either calibrate a instrument or to periodically verify that the instrument is still operating within the tolerances desired, are known to those skilled in the art.

For example, U.S. Pat. No. 3,466,249 (hereinafter referred to as Anderson) discloses a blood serum reference standard comprising a first container of freeze-dried blood serum and a second container of aqueous ammonium bicarbonate. The final pH of Anderson's reconstituted serum is 7.5±0.5. This pH range is felt by Anderson to be within an acceptable range for test systems as well as for stability of the reconstituted serum's components, particularly the enzymes.

U.S. Pat. No. 3,629,142 (hereinafter referred to as Marbach) discloses a freeze-dried serum reference standard comprising blood serum and a carbonate or bicarbonate of tris(hydroxymethyl)aminomethane which is reconstituted by the addition of distilled water. The tris carbonate imparts a normal pH to the serum so as to provide for the stability of its constituents, and particularly the enzymes. (For normal serum and plasma that are collected under routine conditions, the normal pH range is generally considered to be about 7.3 to about 7.45. See Tietz, Fundamental of Clinical Chemistry, W. B. Saunders Co., Philadelphia, Pa. (1970), pg. 634; and Henry et al., Clinical Chemistry, Principles and Technics, 2nd Edition, Harper & Row, New York, N.Y. (1974), pgs. 774-778.)

U.S. Pat. No. 3,876,375 and 4,121,905 (hereinafter referred to Maurukas I and Maurukas II) disclose a biological reference control composition comprising in its non-biological compound from about 60 to about 80 weight percent water and from about 20 to about 40 weight percent of at least one alkylene polyol having from 2 to 5 carbon atoms, the remainder being chiefly at least one natural biological material selected from the group consisting of blood serum, enzyme, metabolites, electrolytes, and hormones. Although the pH of this composition is not disclosed in either Maurukas I or Maurukas II, experiments have shown the pH to be from about 8.3 to about 8.5.

One short coming of the above prior art composition is that their enzyme constituents are highly unstable. For example, the manufacturer of a commercial composition believed to be within the scope of Marbach, supra, recommends that determinations of enzyme constituents of its distilled or deionized water reconstituted serum be made only on the day that the serum is reconstituted.

Similarly, the manufacturer of a commercial composition within the scope of Anderson also recommends that the determinations of its reconstituted composition be made only on the day that the serum is reconstituted.

Both of the above reconstituted compositions are recommended by their manufacturer to be stored between 2° and 8° C.

SUMMARY OF THE INVENTION

The instant invention encompasses an enzyme reference composition having an improved shelf life. The composition comprises at least one enzyme of known value; about 20 to about 40 weight percent of at least one alkylene polyol having from 2 to 5 carbon atoms; about 3 to about 8 gm/dl total protein present is a human serum albumin matrix; and about 60 to about 80 weight percent water.

The enzyme constituents of a composition within the scope of this invention retains 90% of their initial value, based upon an Arrhenius Plot, for the periods set forth in Table I.

TABLE I

ARRHENIUS PLOT FOR 90% LIFE, AT 4° C. STORAGE

| Enzyme Constitution | Shelf-Life | |
|---|---|---|
| Amylase | 6.8 | Years |
| γ-Glutamyl Transpeptidase | 206.9 | Years |
| Lactic Dehydrogenase | 1.0 | Years |
| Creatine Kinase | 145.9 | Years |
| Alkaline Phosphatase | 9.9 | Months |
| Aspartate Amino Transferase | 2.4 | Years |
| Alanine Amino Transferase | 6.6 | Years |

The above Arrhenius Plot shows that the enzyme constituents of the enzyme reference compositions within the scope of this invention are stable for periods of time far exceeding the shelf life of enzyme constituents present in prior art reference compositions.

DESCRIPTION OF THE PREFERRED EMBODIMENTS

The enzyme reference composition of the instant invention comprises at least one enzyme constituent of known value. Any enzyme of clinical significance can be present therein. Typical enzymes which are currently assayed in clinical laboratories include acid phosphatase (ACP); aldolase; alkaline phosphatase (ALP); amylase; cholinesterase; creatine kinase (CK; also known as creatine phosphokinase (CPK)); α-glutamyl transpeptidase (γ-GR; GGT); α-hydroxybutyric dehydrogenase (α-HBD;HBD); isocitric dehydrogenase (ICD); lactic dehydrogenase (LDH); leucine aminopeptidase (LAP); lipase; alanine amino transferase (SGPT; ALT; GPT; glutamic-pyruvic transaminase); and aspartate amino transferase (SGOT; AST: GOT: glutamic-oxalacetic transaminase).

The activity of each enzyme present in the enzyme reference composition is not critical. Preferably, the activity of each enzyme should be within a range covering both normal and abnormal values.

The source of each enzyme is also not critical. However, the preference source of several enzymes are set forth in Table II.

TABLE II

| Enzyme Constituent | Preferred Source |
|---|---|
| ACP | Human Seminal Fluid |
| ALP | Calf Intestine |
| Amylase | Pig Pancreas |
| CK | Monkey Muscle |
| SGOT | Pig Heart |

TABLE II-continued

| Enzyme Constituent | Preferred Source |
| --- | --- |
| SGPT | Pig Heart |
| γ-GT | Pig Intestine |
| LDH | Chicken Heart |

The enzyme reference composition of the instant invention also comprises from about 20 to about 40 weight percent of at least one alkylene polyol having from 2 to 5 carbon atoms. Preferably, the alkylene polyol comprises from about 30 to about 34 weight percent of the enzyme reference composition.

Suitable alkylene polyols which can be used include, but are not limited to, ethylene glycol, propylene glycol, butylene glycol, pentanediol, and glycerol. The alkylene polyol material is preferably selected from a group consisting of ethylene glycol, propylene glycol, glycerol, and mixtures thereof.

The enzyme reference composition of the instant invention also comprises from about 3 to about 8 gm/dl total protein. Preferably, from about 4 to about 5 gm/dl total protein is present in the enzyme reference composition. The total protein is present in a human serum albumin matrix.

The enzyme reference composition of the instant invention also comprises from about 60 to about 80 weight percent water. Preferably, water comprises from about 66 to about 70 weight percent of the enzyme reference composition.

The water can be part of the human serum albumin material and/or can be added as a separate constituent.

The pH of enzyme reference composition of the instant is not critical. The optimum pH of the enzyme reference composition will vary depending upon the particular enzymes present therein. In general, the pH can be from about 5.0 to about 8.7. Preferably, the pH can be from about 6 to about 8.5. More preferably, the pH can be from about 6 to about 7. Usually, the preferred pH will be from about 6.4 to about 6.6. However, ACP has an optional pH of about 6.0.

The pH can be adjusted by any conventional means employed by those skilled in the art, e.g., by the addition of hydrochloric acid (HCl) or sodium hydroxide (NaOH) to the composition.

The enzyme reference composition of the instant invention can also further comprise metabolites, electrolytes, and hormones of known value. Preferably, the enzyme reference composition of the instant invention will further comprise sodium, potassium, calcium, phosphorous, magnesium and chloride in amounts of interest to the clinical chemist.

The enzyme reference composition of the instant invention can be stored in any suitable container, such as a glass ampule.

In general, the enzyme composition of the instant invention can be prepared via the following procedure. A solution having a desired percentage of albumin therein is made by dissolving an appropriate amount of albumin in distilled or deionized water. To this albumin solution is then added a sufficient amount of at least one alkylene polyol having 2 to 5 carbons so that the alkylene polyol-albumin solution comprises from about 20 to about 40 weight percent alkylene polyol, from about 60 to about 80 weight percent water, and from about 3 to about 8 gms/dl total protein in a human serum albumin matrix. The pH of the alkylene polyol-albumin solution is then adjusted to a desirable level. After adjusting the pH, the alkylene polyol-albumin solution is assayed for enzyme activity and salt content to obtain baseline values for each constituent of each of the solution's desired constituents. An amount of each of the constituents is then added to the solution so that the enzymes and salts are present in their desired amount.

If necessary, the pH of the solution is then readjusted to its optimum level with respect to the enzymes present therein.

The stable enzyme reference composition of the instant invention can be employed as an enzyme reference standard or as an enzyme reference control, i.e., the composition can be employed to either calibrate an instrument or can be employed to periodically verify that the instrument is still operating within the tolerances desired. For the above uses, the enzyme reference composition of the instant invention can contain at least one enzyme in amounts typical of those of interest to those in the clinical laboratory.

The following examples are provided for the purpose of further illustration only and are not intended to be limitations of the disclosed invention.

EXAMPLE 1

Table III sets forth one preferred embodiment of the enzyme reference composition of the instant invention wherein the enzyme activity is measured at 37° C.:

TABLE III

| Test | Specification |
| --- | --- |
| ACP | 0–20 IU/l |
| ALP | 0–350 IU/l |
| Amylase | 0–400 IU/l |
| CK | 0–600 IU/l |
| SGOT | 0–200 IU/l |
| SGPT | 0–200 IU/l |
| γ-GT | 0–300 IU/l |
| LDH | 0–500 IU/l |
| Sodium | 125–127 mEq/l |
| Potassium | 3.5–4.5 mEq/l |
| Calcium | 8.4–10.6 mg/dl |
| Phosphorous | 1.6–2.4 mg/dl |
| Magnesium | 1.6–2.4 mg/dl |
| Chloride | 88–112 mEq/l |
| pH | 6.5 ± 0.1 |
| $HB_sAg$-B* | Negative |
| Total Protein (Human Albumin) | 4.5 ± 0.5 gm/dl |
| Ethylene glycol | 33⅓% by weight |
| Water | 66⅔% by weight |

*$Hb_sAg$-B denotes Hepatitis-Surface Antigen Type B

EXAMPLE 2

Preparation of Albumin Base Enzyme Reference Composition

Add albumin (Human Cohn Fraction V) slowly to a 33⅓% by weight aqueous solution of ethylene glycol with continuous mixing. The albumin is preferably dissolved at room temperature, but extended mixing at 2° to 8° C. is acceptable. The amount of albumin added is such that the total protein content is about 4.5±0.5 gm/l.

The pH of the resulting solution is adjusted, if necessary, to 6.5±0.1 with 6 N HCl or 6 N NaOH.

Next, filter the solution through an ethylene glycol impervious filter material having a final filter porosity of 0.4–0.682 .

Assay the filtered solution for enzyme activity and salt content to obtain baseline values for each constituent of the composition. Add an amount of each constituent so that the enzymes and salts are present in amounts within the levels set forth in Table III, supra.

If necessary readjust the pH of the enzyme reference composition to 6.5±0.1 with 6 N HCl or 6 N NaOH.

to the procedure set forth in Example 2, supra, and stored in plastic vials. These compositions were incubated at various temperatures (−15°, 25°, 32°, 37°, and 41° C.) and assayed at 37° C. at designated time intervals. The data obtained are set forth in Tables IV–X.

TABLE IV

ALP

| Hour | 41° C. A | $\frac{A}{E} \times 100\%$ | 37° C. B | $\frac{B}{E} \times 100\%$ | 32° C. C | $\frac{C}{E} \times 100\%$ | 25° C. D | $\frac{D}{E} \times 100\%$ | −15° C. E |
|---|---|---|---|---|---|---|---|---|---|
| 0.0 | 445.0 | 100 | 445.0 | 100 | 445.0 | 100 | 445.0 | 100 | 445.0 |
| 4.0 | 462.0 | 104 | 449.0 | 101 | 455.0 | 102 | 448.0 | 101 | 445.0 |
| 8.0 | 471.0 | 100 | 474.0 | 101 | 479.0 | 102 | 464.0 | 99 | 470.0 |
| 24.0 | 433.0 | 94 | 445.0 | 96 | 460.0 | 100 | 483.0 | 105 | 462.0 |
| 48.0 | 415.0 | 89 | 426.0 | 92 | 448.0 | 97 | 463.0 | 100 | 464.0 |
| 72.0 | 400.0 | 86 | 432.0 | 93 | 444.0 | 95 | 463.0 | 99 | 466.0 |
| 96.0 | 382.0 | 84 | 415.0 | 91 | 435.0 | 95 | 460.0 | 101 | 457.0 |
| 120.0 | 391.0 | 85 | 431.0 | 94 | 445.0 | 97 | 454.0 | 99 | 460.0 |
| 144.0 | 372.0 | 82 | 409.0 | 90 | 420.0 | 93 | 453.0 | 100 | 454.0 |
| 312.0 | 322.0 | 69 | 375.0 | 80 | 415.0 | 88 | 444.0 | 95 | 469.0 |
| 480.0 | 281.0 | 60 | 353.0 | 75 | 398.0 | 85 | 426.0 | 90 | 471.0 |
| 648.0 | 264.0 | 58 | 326.0 | 72 | 378.0 | 84 | 417.0 | 92 | 452.0 |

TABLE V

AMYLASE

| Hour | 41° C. A | $\frac{A}{E} \times 100\%$ | 37° C. B | $\frac{B}{E} \times 100\%$ | 32° C. C | $\frac{C}{E} \times 100\%$ | 25° C. D | $\frac{D}{E} \times 100\%$ | −15° C. E |
|---|---|---|---|---|---|---|---|---|---|
| 0.0 | 420.0 | 100 | 420.0 | 100 | 420.0 | 100 | 420.0 | 100 | 420.0 |
| 4.0 | 412.0 | 98 | 405.0 | 96 | 402.0 | 96 | 412.0 | 98 | 420.0 |
| 8.0 | 380.0 | 95 | 397.0 | 100 | 397.0 | 100 | 382.0 | 96 | 398.0 |
| 24.0 | 361.0 | 95 | 368.0 | 96 | 368.0 | 96 | 381.0 | 100 | 382.0 |
| 48.0 | 362.0 | 91 | 372.0 | 94 | 381.0 | 96 | 379.0 | 95 | 397.0 |
| 72.0 | 354.0 | 89 | 373.0 | 94 | 391.0 | 98 | | N/A | 397.0 |
| 96.0 | 319.0 | 86 | 357.0 | 96 | 369.0 | 99 | | N/A | 371.0 |
| 120.0 | 329.0 | 84 | | N/A[1] | 377.0 | 96 | 386.0 | 99 | 391.0 |
| 312.0 | 295.0 | 75 | 377.0 | 96 | 389.0 | 99 | 394.0 | 101 | 392.0 |
| 480.0 | 291.0 | 74 | 375.0 | 95 | 407.0 | 103 | 382.0 | 97 | 394.0 |
| 648.0 | 306.0 | 75 | 381.0 | 94 | 408.0 | 100 | 414.0 | 102 | 406.0 |

[1]N/A denotes not available.

TABLE VI

CK

| Hour | 41° C. A | $\frac{A}{E} \times 100\%$ | 37° C. B | $\frac{B}{E} \times 100\%$ | 32° C. C | $\frac{C}{E} \times 100\%$ | 25° C. D | $\frac{D}{E} \times 100\%$ | −15° C. E |
|---|---|---|---|---|---|---|---|---|---|
| 0.0 | 559.0 | 100 | 559.0 | 100 | 559.0 | 100 | 599.0 | 100 | 559.0 |
| 4.0 | 543.0 | 97 | 551.0 | 99 | 558.0 | 100 | 533.0 | 99 | 559.0 |
| 8.0 | 515.0 | 93 | 544.0 | 98 | 550.0 | 99 | 559.0 | 101 | 554.0 |
| 24.0 | 417.0 | 75 | 514.0 | 92 | 544.0 | 98 | 549.0 | 99 | 557.0 |
| 48.0 | 300.0 | 54 | 474.0 | 86 | 529.0 | 95 | 554.0 | 100 | 554.0 |
| 72.0 | 207.0 | 38 | 450.0 | 83 | 517.0 | 95 | 524.0 | 97 | 543.0 |
| 96.0 | | N/A[1] | 410.0 | 76 | 499.0 | 93 | 534.0 | 99 | 539.0 |
| 120.0 | | N/A | 408.0 | 73 | 519.0 | 92 | 527.0 | 94 | 562.0 |
| 144.0 | | N/A | 377.0 | 68 | 507.0 | 92 | 552.0 | 100 | 551.0 |
| 312.0 | | N/A | 259.0 | 46 | 476.0 | 85 | 543.0 | 97 | 559.0 |
| 480.0 | | N/A | | N/A | 445.0 | 80 | 538.0 | 96 | 558.0 |
| 648.0 | | N/A | | N/A | 415.0 | 74 | 503.0 | 90 | 558.0 |

[1]N/A denotes not available.

EXAMPLE 3

One lot of enzyme reference composition within the scope of the instant invention was formulated according

TABLE VII

SGOT

| Hour | 41° C. A | $\frac{A}{E} \times 100\%$ | 37° C. B | $\frac{B}{E} \times 100\%$ | 32° C. C | $\frac{C}{E} \times 100\%$ | 25° C. D | $\frac{D}{E} \times 100\%$ | −15° C. E |
|---|---|---|---|---|---|---|---|---|---|
| 0.0 | 464.0 | 100 | 464.0 | 100 | 464.0 | 100 | 464.0 | 100 | 464.0 |
| 4.0 | 463.0 | 100 | 458.0 | 99 | 467.0 | 101 | 460.0 | 99 | 464.0 |
| 8.0 | 454.0 | 99 | 459.0 | 100 | 458.0 | 100 | 462.0 | 100 | 460.0 |
| 24.0 | 439.0 | 96 | 449.0 | 98 | 454.0 | 99 | 453.0 | 99 | 457.0 |

TABLE VII-continued

SGOT

| Hour | 41° C. A | $\frac{A}{E} \times 100\%$ | 37° C. B | $\frac{B}{E} \times 100\%$ | 32° C. C | $\frac{C}{E} \times 100\%$ | 25° C. D | $\frac{D}{E} \times 100\%$ | −15° C. E |
|---|---|---|---|---|---|---|---|---|---|
| 48.0 | 421.0 | 92 | 435.0 | 95 | 449.0 | 98 | 459.0 | 100 | 460.0 |
| 72.0 | 418.0 | 88 | 456.0 | 96 | 466.0 | 98 | 467.0 | 99 | 474.0 |
| 96.0 | 389.0 | 82 | 428.0 | 90 | 451.0 | 95 | 472.0 | 100 | 474.0 |
| 120.0 | 368.0 | 79 | 413.0 | 89 | 439.0 | 94 | 448.0 | 96 | 466.0 |
| 144.0 | 347.0 | 75 | 395.0 | 85 | 426.0 | 92 | 455.0 | 98 | 462.0 |
| 312.0 | 238.0 | 51 | 321.0 | 69 | 388.0 | 83 | 439.0 | 94 | 466.0 |
| 480.0 | 153.0 | 33 | 254.0 | 55 | 346.0 | 74 | 423.0 | 91 | 465.0 |
| 648.0 | | N/A[1] | 290.0 | 45 | 313.0 | 68 | 408.0 | 88 | 462.0 |

[1]N/A denotes not available.

TABLE VIII

SGPT

| Hour | 41° C. A | $\frac{A}{E} \times 100\%$ | 37° C. B | $\frac{B}{E} \times 100\%$ | 32° C. C | $\frac{C}{E} \times 100\%$ | 25° C. D | $\frac{D}{E} \times 100\%$ | −15° C. E |
|---|---|---|---|---|---|---|---|---|---|
| 0.0 | 522.0 | 100 | 522.0 | 100 | 522.0 | 100 | 552.0 | 100 | 522.0 |
| 4.0 | 509.0 | 98 | 517.0 | 99 | 517.0 | 99 | 519.0 | 99 | 522.0 |
| 8.0 | 473.0 | 91 | 478.0 | 92 | 493.0 | 95 | 511.0 | 98 | 521.0 |
| 24.0 | 438.0 | 84 | 475.0 | 91 | 488.0 | 94 | 511.0 | 98 | 521.0 |
| 48.0 | 418.0 | 78 | 458.0 | 86 | 488.0 | 92 | 514.0 | 96 | 533.0 |
| 72.0 | 369.0 | 74 | 418.0 | 84 | 466.0 | 94 | | N/A[1] | —496.0 |
| 96.0 | 357.0 | 68 | 418.0 | 80 | 474.0 | 90 | 508.0 | 97 | 525.0 |
| 120.0 | 329.0 | 66 | 411.0 | 83 | 453.0 | 91 | 487.0 | 98 | 497.0 |

[1]N/A denotes not available.

TABLE IX

γ-GT

| Hour | 41° C. A | $\frac{A}{E} \times 100\%$ | 37° C. B | $\frac{B}{E} \times 100\%$ | 32° C. C | $\frac{C}{E} \times 100\%$ | 25° C. D | $\frac{D}{E} \times 100\%$ | −15° C. E |
|---|---|---|---|---|---|---|---|---|---|
| 0.0 | 139.0 | 100 | 139.0 | 100 | 139.0 | 100 | 139.0 | 100 | 139.0 |
| 4.0 | 139.0 | 100 | 136.0 | 98 | 139.0 | 100 | 143.0 | 103 | 139.0 |
| 8.0 | 138.0 | 101 | 140.0 | 102 | 137.0 | 100 | 139.0 | 101 | 137.0 |
| 24.0 | 133.0 | 96 | 137.0 | 99 | 133.0 | 96 | 139.0 | 101 | 138.0 |
| 48.0 | 135.0 | 98 | 136.0 | 99 | 138.0 | 100 | 138.0 | 100 | 138.0 |
| 72.0 | 135.0 | 96 | 143.0 | 101 | 143.0 | 101 | 140.0 | 99 | 141.0 |
| 96.0 | 136.0 | 97 | 142.0 | 101 | 142.0 | 101 | 142.0 | 101 | 140.0 |
| 120.0 | 142.0 | 96 | 148.0 | 100 | 146.0 | 99 | 143.0 | 97 | 148.0 |
| 144.0 | 137.0 | 98 | 141.0 | 101 | 139.0 | 99 | 144.0 | 103 | 140.0 |
| 312.0 | 129.0 | 91 | 135.0 | 96 | 139.0 | 99 | 141.0 | 100 | 141.0 |
| 480.0 | 124.0 | 91 | 133.0 | 97 | 136.0 | 99 | 137.0 | 100 | 137.0 |
| 648.0 | 121.0 | 89 | 132.0 | 97 | 136.0 | 100 | 136.0 | 100 | 136.0 |

TABLE X

LDH

| Hour | 41° C. A | $\frac{A}{E} \times 100\%$ | 37° C. B | $\frac{B}{E} \times 100\%$ | 32° C. C | $\frac{C}{E} \times 100\%$ | 25° C. D | $\frac{D}{E} \times 100\%$ | −15° C. E |
|---|---|---|---|---|---|---|---|---|---|
| 0.0 | 662.0 | 100 | 662.0 | 100 | 662.0 | 100 | 662.0 | 100 | 662.0 |
| 4.0 | 652.0 | 98 | 655.0 | 99 | 651.0 | 98 | 651.0 | 98 | 662.0 |
| 8.0 | 617.0 | 97 | 623.0 | 98 | 626.0 | 99 | 633.0 | 100 | 633.0 |
| 24.0 | 591.0 | 94 | 603.0 | 96 | 609.0 | 97 | 622.0 | 99 | 627.0 |
| 48.0 | 585.0 | 94 | 604.0 | 97 | 609.0 | 98 | 608.0 | 98 | 621.0 |
| 72.0 | 555.0 | 92 | 556.0 | 93 | 584.0 | 97 | 590.0 | 98 | 601.0 |
| 96.0 | 563.0 | 91 | 585.0 | 95 | 597.0 | 96 | 612.0 | 99 | 619.0 |
| 120.0 | 553.0 | 89 | 572.0 | 92 | 593.0 | 96 | 601.0 | 97 | 619.0 |

Table XI sets forth an Arrhenius Plot for 90% life based upon the data set forth in Tables IV–X.

TABLE XI

ARRHENIUS PLOT FOR 90% LIFE BASED ON TEMPERATURES 41°, 37°, 32°, AND 25° C.

| Temperature | ALP | Amylase | CK | SGOT | SGPT | γ-GT | LDH |
|---|---|---|---|---|---|---|---|
| 4° C. | 9.9M[1] | 6.8 Y | 145.9 Y | 2.4 Y | 6.6 Y | 206.9 Y | 1.0 Y |

TABLE XI-continued

ARRHENIUS PLOT FOR 90% LIFE
BASED ON TEMPERATURES 41°, 37°, 32°, AND 25° C.

| Temperature | ALP | Amylase | CK | SGOT | SGPT | γ-GT | LDH |
|---|---|---|---|---|---|---|---|
| −15° C. | 10.2 Y[2] | 132.1 Y | 208452.5 Y | 109.8 Y | 734.9 Y | N/A[3] | 14.8 Y |

[1]M denotes months
[2]Y denotes years
[3]N/A denotes not available

The data in Tables IV–X as well as Table XI's Arrhenius Plot based thereon demonstrate that the enzyme reference compositions within the scope of this invention are stable for periods of time far exceeding the shelf life of enzyme constituents present in prior art reference compositions.

The following examples are provided for the purpose of distinguishing the instant invention over the invention set forth in Maurukas I and Maurukas II, supra.

EXAMPLE 4

Lots of enzyme reference compositions within the scope of the instant invention were formulated according to the procedure set forth in Example 2, supra, save that when the pH of a particular lot was other than 6.5±0.1, that lot's pH was adjusted accordingly with either 6 N HCl or 6 N NaOH. These lots were stored in plastic vials, incubated at various temperatures, and assayed at 37° C. at designated time intervals. The data obtained are set forth in Tables XII–XXI.

TABLE XII

ALP @ pH 6.5 in Human Serum Albumin Matrix

| Hour | 41° C. A | $\frac{A}{E} \times 100\%$ | 37° C. B | $\frac{B}{E} \times 100\%$ | 32° C. C | $\frac{C}{E} \times 100\%$ | 25° C. D | $\frac{D}{E} \times 100\%$ | −15° C. E |
|---|---|---|---|---|---|---|---|---|---|
| 0.0 | 107.0 | 100 | 107.0 | 100 | 107.0 | 100 | 107.0 | 100 | 107.0 |
| 4.0 | 110.0 | 103 | 167.0 | 156 | 109.0 | 102 | 108.0 | 101 | 107.0 |
| 8.0 | 113.0 | 97 | 115.0 | 99 | 115.0 | 99 | 111.0 | 96 | 116.0 |
| 24.0 | 103.0 | 96 | 106.0 | 99 | 109.0 | 102 | 107.0 | 100 | 107.0 |
| 48.0 | 101.0 | 89 | 106.0 | 93 | 107.0 | 94 | 110.0 | 96 | 114.0 |
| 72.0 | 98.0 | 89 | 103.0 | 94 | 108.0 | 98 | 112.0 | 102 | 110.0 |
| 96.0 | 94.0 | 84 | 100.0 | 89 | 104.0 | 93 | 110.0 | 98 | 112.0 |
| 120.0 | 95.0 | 81 | 104.0 | 89 | 105.0 | 90 | 106.0 | 91 | 117.0 |
| 144.0 | 88.0 | 78 | 99.0 | 88 | 102.0 | 90 | 109.0 | 96 | 113.0 |
| 312.0 | 78.0 | 68 | 94.0 | 82 | 100.0 | 88 | 108.0 | 95 | 114.0 |
| 480.0 | 70.0 | 64 | 85.0 | 77 | 94.0 | 85 | 103.0 | 94 | 110.0 |
| 648.0 | 66.0 | 60 | 77.0 | 70 | 89.0 | 81 | 97.0 | 88 | 110.0 |

TABLE XII

ALP @ pH 6.5 in Human Serum Albumin Matrix

| Hour | 41° C. A | $\frac{A}{D} \times 100\%$ | 37° C. B | $\frac{B}{D} \times 100\%$ | 32° C. C | $\frac{C}{D} \times 100\%$ | −15° C. D |
|---|---|---|---|---|---|---|---|
| 0.0 | 686.0 | 100 | 686.0 | 100 | 686.0 | 100 | 686.0 |
| 4.0 | 719.0 | 105 | 672.0 | 98 | 679.0 | 99 | 686.0 |
| 8.0 | 744.0 | 99 | 727.0 | 96 | 826.0 | 109 | 755.0 |
| 72.0 | 740.0 | 98 | 787.0 | 104 | 788.0 | 104 | 755.0 |
| 96.0 | 754.0 | 97 | 822.0 | 106 | 801.0 | 103 | 744.0 |
| 168.0 | N/A[1] | | 744.0 | 99 | N/A | | 748.0 |

[1]N/A denotes not available.

TABLE XIV

CK @ pH 6.5 in Human Serum Albumin Matrix

| Hour | 41° C. A | $\frac{A}{E} \times 100\%$ | 37° C. B | $\frac{B}{E} \times 100\%$ | 32° C. C | $\frac{C}{E} \times 100\%$ | 25° C. D | $\frac{D}{E} \times 100\%$ | −15° C. E |
|---|---|---|---|---|---|---|---|---|---|
| 0.0 | 340.0 | 100 | 340.0 | 100 | 340.0 | 100 | 340.0 | 100 | 340.0 |
| 4.0 | 330.0 | 97 | 325.0 | 96 | 335.0 | 99 | 332.0 | 98 | 340.0 |
| 8.0 | 309.9 | 93 | 310.0 | 93 | 335.0 | 101 | 337.0 | 101 | 333.0 |
| 24.0 | 249.0 | 75 | 305.0 | 91 | 322.0 | 96 | 331.0 | 99 | 334.0 |
| 48.0 | 184.0 | 55 | 285.0 | 85 | 316.0 | 94 | 330.0 | 99 | 335.0 |
| 72.0 | 130.0 | 39 | 268.0 | 80 | 312.0 | 94 | 321.0 | 96 | 333.0 |
| 96.0 | | N/A[1] | 248.0 | 76 | 298.0 | 92 | 319.0 | 98 | 325.0 |
| 120.0 | | N/A | 245.0 | 72 | 312.0 | 91 | 324.0 | 95 | 342.0 |
| 144.0 | | N/A | 231.0 | 70 | 303.0 | 91 | 328.0 | 99 | 332.0 |

[1]N/A denotes not available.

TABLE XV

CK @ pH 8.5 in Human Serum Albumin Matrix

| | 41° C. | | | 37° C. | | | 32° C. | | −15° C. |
|---|---|---|---|---|---|---|---|---|---|
| Hour | A | $\frac{A}{D} \times 100\%$ | B | $\frac{B}{D} \times 100\%$ | | C | $\frac{C}{D} \times 100\%$ | | D |
| 0.0 | 464.0 | 100 | 464.0 | 100 | | 464.0 | 100 | | 464.0 |
| 4.0 | 440.0 | 95 | 481.0 | 104 | | 451.0 | 97 | | 464.0 |
| 8.0 | 315.0 | 65 | 425.0 | 88 | | 507.0 | 105 | | 485.0 |
| 24.0 | 62.0 | 13 | 303.0 | 65 | | 415.0 | 89 | | 466.0 |
| 48.0 | N/A[1] | | 209.0 | 43 | | 393.0 | 81 | | 483.0 |
| 72.0 | N/A | | N/A | | | N/A | | | 485.0 |
| 96.0 | N/A | | N/A | | | 317.0 | 70 | | 450.0 |
| 168.0 | N/A | | N/A | | | 445.0 | 92 | | 482.0 |
| 336.0 | N/A | | N/A | | | 201.0 | 43 | | 465.0 |

[1]N/A denotes not available.

TABLE XVI

SGOT @ pH 6.0 in Human Serum Albumin Matrix

| | 41° C. | | 37° C. | | 32° C. | | 25° C. | | −15° C. |
|---|---|---|---|---|---|---|---|---|---|
| Hour | A | $\frac{A}{E} \times 100\%$ | B | $\frac{B}{E} \times 100\%$ | C | $\frac{C}{E} \times 100\%$ | D | $\frac{D}{E} \times 100\%$ | E |
| 0.0 | 194.0 | 100 | 194.0 | 100 | 194.0 | 100 | 194.0 | 100 | 194.0 |
| 24.0 | 187.0 | 96 | 189.0 | 97 | 191.0 | 98 | 192.0 | 99 | 194.0 |
| 48.0 | 179.0 | 92 | 186.0 | 96 | 191.0 | 98 | 190.0 | 98 | 194.0 |
| 168.0 | 153.0 | 79 | 169.0 | 87 | 178.0 | 92 | 186.0 | 96 | 194.0 |

TABLE XVII

SGOT @ pH 8.5 in Human Serum Albumin Matrix

| | 41° C. | | 37° C. | | 32° C. | | −15° C. |
|---|---|---|---|---|---|---|---|
| Hour | A | $\frac{A}{D} \times 100\%$ | B | $\frac{B}{D} \times 100\%$ | C | $\frac{C}{D} \times 100\%$ | D |
| 0.0 | 288.0 | 100 | 288.0 | 100 | 288.0 | 100 | 288.0 |
| 4.0 | 289.0 | 100 | 279.0 | 97 | 276.0 | 96 | 288.0 |
| 8.0 | 273.0 | 98 | 272.0 | 98 | 286.0 | 103 | 278.0 |
| 24.0 | 301.0 | 99 | 304.0 | 100 | 298.0 | 98 | 305.0 |
| 48.0 | 286.0 | 99 | 288.0 | 99 | 244.0 | 84 | 290.0 |
| 72.0 | 291.0 | 98 | 290.0 | 97 | 293.0 | 98 | 298.0 |
| 96.0 | 294.0 | 98 | 295.0 | 99 | 294.0 | 98 | 299.0 |
| 168.0 | N/A[1] | | 300.0 | 99 | 246.0 | 81 | 304.0 |
| 336.0 | N/A | | 271.0 | 93 | 280.0 | 96 | 292.0 |

[1]N/A denotes not available.

TABLE XVIII

SGPT @ pH 6.0 in Human Serum Albumin Matrix

| | 41° C. | | 37° C. | | 32° C. | | 25° C. | | −15° C. |
|---|---|---|---|---|---|---|---|---|---|
| Hour | A | $\frac{A}{E} \times 100\%$ | B | $\frac{B}{E} \times 100\%$ | C | $\frac{C}{E} \times 100\%$ | D | $\frac{D}{E} \times 100\%$ | E |
| 0.0 | 30.0 | 100 | 30.0 | 100 | 30.0 | 100 | 30.0 | 100 | 30.0 |
| 8.0 | 28.0 | 93 | 30.0 | 100 | 31.0 | 103 | 32.0 | 107 | 30.0 |
| 24.0 | 29.0 | 97 | 32.0 | 107 | 30.0 | 100 | 31.0 | 103 | 30.0 |
| 48.0 | 26.0 | 87 | 28.0 | 93 | 30.0 | 100 | 31.0 | 103 | 30.0 |
| 168.0 | 22.0 | 73 | 25.0 | 83 | 26.0 | 87 | 29.0 | 97 | 30.0 |

TABLE XIX

SGPT @ pH 8.5 in Human Serum Albumin Matrix

| | 41° C. | | 37° C. | | 32° C. | | −15° C. |
|---|---|---|---|---|---|---|---|
| Hour | A | $\frac{A}{D} \times 100\%$ | B | $\frac{B}{D} \times 100\%$ | C | $\frac{C}{D} \times 100\%$ | D |
| 0.0 | 255.0 | 100 | 255.0 | 100 | 255.0 | 100 | 255.0 |
| 4.0 | 250.0 | 98 | 239.0 | 94 | 246.0 | 96 | 255.0 |
| 8.0 | 218.0 | 94 | 216.0 | 94 | 246.0 | 106 | 231.0 |
| 24.0 | 191.0 | 79 | 215.0 | 89 | 222.0 | 92 | 241.0 |
| 48.0 | 150.0 | 70 | 193.0 | 91 | 218.0 | 102 | 213.0 |
| 72.0 | 140.0 | 56 | 201.0 | 80 | 227.0 | 91 | 250.0 |
| 96.0 | 107.0 | 46 | 175.0 | 75 | 206.0 | 88 | 234.0 |
| 168.0 | N/A[1] | | 140.0 | 63 | 209.0 | 95 | 221.0 |
| 336.0 | N/A | | 29.0 | 14 | 75.0 | 35 | 213.0 |

[1]N/A denotes not available.

TABLE XX

LDH @ pH 6.5 in Human Serum Albumin Matrix

| Hour | 41° C. | | 37° C. | | 32° C. | | −15° C. |
|---|---|---|---|---|---|---|---|
| | A | $\frac{A}{D} \times 100\%$ | B | $\frac{B}{D} \times 100\%$ | C | $\frac{C}{D} \times 100\%$ | D |
| 0.0 | 416.0 | 100 | 416.0 | 100 | 416.0 | 100 | 416.0 |
| 4.0 | 402.0 | 97 | 407.0 | 98 | 410.0 | 99 | 416.0 |
| 8.0 | 407.0 | 104 | 408.0 | 104 | 410.0 | 105 | 392.0 |
| 24.0 | 447.0 | 112 | 492.0 | 123 | 483.0 | 121 | 400.0 |
| 48.0 | 378.0 | 92 | 394.0 | 96 | 394.0 | 96 | 411.0 |
| 72.0 | 420.0 | 91 | 432.0 | 94 | 460.0 | 100 | 461.0 |
| 96.0 | 346.0 | 85 | 378.0 | 93 | 396.0 | 98 | 406.0 |
| 168.0 | 381.0 | 85 | | N/A[1] | 417.0 | 93 | 447.0 |
| 336.0 | 343.0 | 83 | 370.0 | 90 | 377.0 | 92 | 411.0 |
| 505.0 | 360.0 | 84 | 372.0 | 87 | 394.0 | 92 | 427.0 |

[1]N/A denotes not available.

TABLE XXI

LDH @ pH in Human Serum Albumin Matrix

| Hour | 41° C. | | 37° C. | | 32° C. | | −15° C. |
|---|---|---|---|---|---|---|---|
| | A | $\frac{A}{D} \times 100\%$ | B | $\frac{B}{D} \times 100\%$ | C | $\frac{C}{D} \times 100\%$ | D |
| 0.0 | 402.0 | 100 | 402.0 | 100 | 402.0 | 100 | 402.0 |
| 4.0 | 395.0 | 98 | 393.0 | 98 | 397.0 | 99 | 402.0 |
| 8.0 | 380.0 | 96 | 385.0 | 97 | 402.0 | 101 | 397.0 |
| 24.0 | 425.0 | 108 | 442.0 | 113 | 456.0 | 116 | 392.0 |
| 48.0 | 359.0 | 89 | 375.0 | 93 | 382.0 | 95 | 403.0 |
| 72.0 | 400.0 | 89 | 422.0 | 94 | 434.0 | 96 | 450.0 |
| 96.0 | 338.0 | 87 | 359.0 | 93 | 374.0 | 97 | 387.0 |
| 168.0 | 380.0 | 85 | 389.0 | 87 | 417.0 | 93 | 448.0 |
| 336.0 | | N/A[1] | 347.0 | 88 | 360.0 | 91 | 395.0 |

[1]N/A denotes not available.

EXAMPLE 5

Lots of enzyme reference compositions of the type described by Maurukas I and Maurukas II, supra, were formulated according to the improved procedure set forth in U.S. Pat. No. 4,158,544. These lots were stored in plastic vials, incubated at various temperatures, and assayed at 37° C. at designated time intervals. The data obtained are set forth in Tables XXII–XXXI.

TABLE XXII

ALP @ pH 6.5 in Human Serum Matrix

| Hour | 41° C. | | 37° C. | | 32° C. | | −15° C. |
|---|---|---|---|---|---|---|---|
| | A | $\frac{A}{D} \times 100\%$ | B | $\frac{B}{D} \times 100\%$ | C | $\frac{C}{D} \times 100\%$ | D |
| 0.0 | 51.0 | 100 | 51.0 | 100 | 51.0 | 100 | 51.0 |
| 4.0 | 54.0 | 106 | 54.0 | 106 | 54.0 | 106 | 51.0 |
| 8.0 | 57.0 | 112 | 56.0 | 110 | 55.0 | 108 | 51.0 |
| 24.0 | 50.0 | 94 | 54.0 | 102 | 57.0 | 108 | 53.0 |
| 48.0 | 47.0 | 85 | 51.0 | 93 | 57.0 | 104 | 55.0 |
| 72.0 | 37.0 | 70 | 46.0 | 87 | 52.0 | 98 | 53.0 |
| 96.0 | 34.0 | 64 | 43.0 | 81 | 50.0 | 94 | 53.0 |
| 121.0 | 33.0 | 60 | 43.0 | 78 | 51.0 | 93 | 55.0 |
| 144.0 | 30.0 | 55 | 42.0 | 76 | 48.0 | 87 | 55.0 |
| 336.0 | 18.0 | 35 | 31.0 | 60 | 39.0 | 75 | 52.0 |
| 504.0 | | N/A[1] | 32.0 | 55 | 43.0 | 74 | 58.0 |
| 1344.0 | | N/A | 24.0 | 35 | 43.0 | 62 | 69.0 |
| 2016.0 | | N/A | | N/A | 29.0 | 51 | 57.0 |

[1]N/A denotes not available.

TABLE XXIII

ALP @ pH 8.5 in Human Serum Matrix

| Hour | 41° C. | | 37° C. | | 32° C. | | −15° C. |
|---|---|---|---|---|---|---|---|
| | A | $\frac{A}{D} \times 100\%$ | B | $\frac{B}{D} \times 100\%$ | C | $\frac{C}{D} \times 100\%$ | D |
| 0.0 | 295.0 | 100 | 295.0 | 100 | 295.0 | 100 | 295.0 |
| 4.0 | 298.0 | 101 | 295.0 | 100 | 294.0 | 100 | 295.0 |
| 8.0 | 288.0 | 99 | 309.0 | 106 | 309.0 | 106 | 291.0 |
| 24.0 | 263.0 | 89 | | N/A[1] | 292.0 | 99 | 294.0 |
| 48.0 | 235.0 | 76 | 283.0 | 92 | 292.0 | 94 | 309.0 |
| 72.0 | 223.0 | 77 | 295.0 | 102 | 312.0 | 108 | 289.0 |
| 96.0 | 187.0 | 64 | 274.0 | 94 | 302.0 | 103 | 293.0 |
| 172.0 | 114.0 | 39 | 220.0 | 75 | 258.0 | 88 | 293.0 |

[1]N/A denotes not available.

TABLE XXIV

CK @ pH 6.5 in Human Serum Matrix

| Hour | 41° C. A | $\frac{A}{D} \times 100\%$ | 37° C. B | $\frac{B}{D} \times 100\%$ | 32° C. C | $\frac{C}{D} \times 100\%$ | −15° C. D |
|---|---|---|---|---|---|---|---|
| 0.0 | 278.0 | 100 | 278.0 | 100 | 278.0 | 100 | 278.0 |
| 4.0 | 286.0 | 103 | 285.0 | 103 | 281.0 | 101 | 278.0 |
| 8.0 | 260.0 | 87 | 261.0 | 87 | 263.0 | 88 | 300.0 |
| 24.0 | 210.0 | 73 | 261.0 | 90 | 272.0 | 94 | 289.0 |
| 48.0 | 156.0 | 53 | 252.0 | 86 | 269.0 | 92 | 293.0 |
| 72.0 | N/A[1] | | 238.0 | 83 | 260.0 | 90 | 288.0 |
| 96.0 | N/A | | 213.0 | 73 | 247.0 | 85 | 292.0 |
| 121.0 | N/A | | 195.0 | 66 | 241.0 | 82 | 294.0 |
| 144.0 | N/A | | 183.0 | 62 | 236.0 | 80 | 294.0 |
| 336.0 | N/A | | 101.0 | 40 | 167.0 | 65 | 255.0 |
| 504.0 | N/A | | N/A | | 157.0 | 58 | 270.0 |

[1]N/A denotes not available.

TABLE XXV

CK @ pH 8.5 in Human Serum Matrix

| Hour | 41° C. A | $\frac{A}{D} \times 100\%$ | 37° C. B | $\frac{B}{D} \times 100\%$ | 32° C. C | $\frac{C}{D} \times 100\%$ | −15° C. D |
|---|---|---|---|---|---|---|---|
| 0.0 | 127.0 | 100 | 127.0 | 100 | 127.0 | 100 | 127.0 |
| 4.0 | 115.0 | 91 | 129.0 | 102 | 124.0 | 98 | 127.0 |
| 8.0 | 71.0 | 55 | 119.0 | 93 | 132.0 | 103 | 128.0 |
| 24.0 | 2.0 | 2 | N/A[1] | | 99.0 | 85 | 117.0 |
| 48.0 | N/A | | 28.0 | 24 | 83.0 | 71 | 117.0 |
| 72.0 | N/A | | N/A | | 68.0 | 56 | 122.0 |
| 96.0 | N/A | | N/A | | 56.0 | 43 | 131.0 |

[1]N/A denotes not available.

TABLE XXVI

SGOT @ pH 6.0 in Human Serum Matrix

| Hour | 41° C. A | $\frac{A}{D} \times 100\%$ | 25° C. B | $\frac{B}{D} \times 100\%$ | 4° C. C | $\frac{C}{D} \times 100\%$ | −15° C. D |
|---|---|---|---|---|---|---|---|
| 0.0 | 111.0 | 100 | 111.0 | 100 | 111.0 | 100 | 111.0 |
| 1.0 | 110.0 | 99 | N/A[1] | | N/A | | 111.0 |
| 2.0 | 111.0 | 100 | N/A | | N/A | | 111.0 |
| 3.0 | 109.0 | 98 | N/A | | N/A | | 111.0 |
| 4.0 | 107.0 | 96 | 112.0 | 101 | 111.0 | 100 | 111.0 |
| 5.0 | 121.0 | 102 | N/A | | N/A | | 118.0 |
| 6.0 | 114.0 | 96 | N/A | | N/A | | 118.0 |
| 7.0 | 111.0 | 94 | N/A | | N/A | | 118.0 |
| 8.0 | 106.0 | 90 | N/A | | N/A | | 118.0 |
| 9.0 | 103.0 | 87 | 121.0 | 102 | 118.0 | 100 | 118.0 |
| 10.0 | 86.0 | 76 | N/A | | N/A | | 114.0 |
| 11.0 | 87.0 | 77 | N/A | | N/A | | 114.0 |
| 12.0 | 91.0 | 80 | N/A | | N/A | | 114.0 |
| 15.0 | 79.0 | 70 | 108.0 | 96 | 112.0 | 99 | 113.0 |
| 24.0 | 49.0 | 43 | 108.0 | 95 | 113.0 | 100 | 114.0 |
| 30.0 | 43.0 | 38 | N/A | | N/A | | 113.0 |
| 36.0 | 36.0 | 32 | 103.0 | 91 | 112.0 | 99 | 113.0 |
| 48.0 | 22.0 | 20 | 98.0 | 88 | 111.0 | 99 | 112.0 |
| 56.0 | 17.0 | 15 | 98.0 | 87 | 112.0 | 99 | 113.0 |
| 72.0 | < 5.0 | N/A | 95.0 | 84 | 112.0 | 99 | 114.0 |
| 80.0 | < 5.0 | N/A | 93.0 | 83 | 112.0 | 100 | 113.0 |

[1]N/A denotes not available.

TABLE XXVII

SGOT @ pH 8.5 in Human Serum Matrix

| Hour | 41° C. A | $\frac{A}{D} \times 100\%$ | 25° C. B | $\frac{B}{D} \times 100\%$ | 4° C. C | $\frac{C}{D} \times 100\%$ | −15° C. D |
|---|---|---|---|---|---|---|---|
| 0.0 | 124.0 | 100 | 124.0 | 100 | 124.0 | 100 | 124.0 |
| 1.0 | 124.0 | 99 | N/A[1] | | N/A | | 124.0 |
| 2.0 | 125.0 | 101 | N/A | | N/A | | 124.0 |
| 3.0 | 123.0 | 99 | N/A | | N/A | | 124.0 |
| 4.0 | 123.0 | 99 | 124.0 | 100 | 124.0 | 100 | 124.0 |
| 5.0 | 136.0 | 103 | N/A | | N/A | | 132.0 |
| 6.0 | 135.0 | 102 | N/A | | N/A | | 132.0 |
| 7.0 | 132.0 | 100 | N/A | | N/A | | 132.0 |
| 8.0 | 130.0 | 98 | N/A | | N/A | | 132.0 |

TABLE XXVII-continued

| | SGOT @ pH 8.5 in Human Serum Matrix | | | | | | |
|---|---|---|---|---|---|---|---|
| | 41° C. | | 25° C. | | 4° C. | | −15° C. |
| Hour | A | $\frac{A}{D} \times 100\%$ | B | $\frac{B}{D} \times 100\%$ | C | $\frac{C}{D} \times 100\%$ | D |
| 9.0 | 129.0 | 98 | 132.0 | 100 | 130.0 | 98 | 132.0 |
| 10.0 | 117.0 | 92 | | N/A | | N/A | 127.0 |
| 11.0 | 117.0 | 92 | | N/A | | N/A | 127.0 |
| 12.0 | 121.0 | 95 | | N/A | | N/A | 127.0 |
| 15.0 | 122.0 | 96 | 120.0 | 94 | 125.0 | 98 | 128.0 |
| 24.0 | 111.0 | 87 | 126.0 | 99 | 127.0 | 100 | 127.0 |
| 30.0 | 107.0 | 85 | | N/A | | N/A | 126.0 |
| 36.0 | 101.0 | 80 | 125.0 | 99 | 126.0 | 100 | 126.0 |
| 48.0 | 90.0 | 71 | 124.0 | 98 | 126.0 | 100 | 126.0 |
| 56.0 | 80.0 | 63 | 124.0 | 98 | 126.0 | 100 | 127.0 |
| 72.0 | 64.0 | 50 | 123.0 | 96 | 127.0 | 99 | 128.0 |
| 80.0 | 59.0 | 46 | 123.0 | 96 | 127.0 | 100 | 128.0 |

[1]N/A denotes not available.

TABLE XXVIII

| | SGPT @ pH 6.0 in Human Serum Matrix | | | | | | |
|---|---|---|---|---|---|---|---|
| | 41° C. | | 25° C. | | 4° C. | | −15° C. |
| Hour | A | $\frac{A}{D} \times 100\%$ | B | $\frac{B}{D} \times 100\%$ | C | $\frac{C}{D} \times 100\%$ | D |
| 0.0 | 16.0 | 102 | 16.0 | 102 | 16.0 | 102 | 16.0 |
| 1.0 | 18.0 | 115 | | N/A[1] | | N/A | 16.0 |
| 2.0 | 19.0 | 121 | | N/A | | N/A | 16.0 |
| 3.0 | 20.0 | 128 | | N/A | | N/A | 16.0 |
| 4.0 | 20.0 | 100 | 18.0 | 90 | 20.0 | 100 | 20.0 |
| 5.0 | 12.0 | 68 | | N/A | | N/A | 18.0 |
| 6.0 | 13.0 | 74 | | N/A | | N/A | 18.0 |
| 7.0 | 14.0 | 80 | | N/A | | N/A | 18.0 |
| 8.0 | 15.0 | 85 | | N/A | | N/A | 18.0 |
| 9.0 | 17.0 | 97 | 18.0 | 102 | 17.0 | 97 | 18.0 |
| 10.0 | 22.0 | 90 | | N/A | | N/A | 24.0 |
| 11.0 | 7.0 | 29 | | N/A | | N/A | 24.0 |
| 12.0 | 29.0 | 119 | | N/A | | N/A | 24.0 |
| 15.0 | 15.0 | 88 | 16.0 | 94 | 17.0 | 100 | 17.0 |
| 24.0 | 11.0 | 45 | 29.0 | 119 | 13.0 | 53 | 24.0 |
| 30.0 | 12.0 | 72 | | N/A | | N/A | 17.0 |
| 36.0 | 10.0 | 60 | 16.0 | 95 | 17.0 | 101 | 17.0 |
| 48.0 | 8.0 | 47 | 16.0 | 94 | 16.0 | 94 | 17.0 |
| 56.0 | 8.0 | 42 | 16.0 | 84 | 17.0 | 89 | 19.0 |
| 72.0 | 7.0 | 41 | 16.0 | 95 | 17.0 | 101 | 17.0 |
| 80.0 | <5.0 | N/A | 16.0 | 104 | 17.0 | 111 | 15.0 |

[1]N/A denotes not available.

TABLE XXIX

| | SGPT @ pH 8.5 in Human Serum Matrix | | | | | | |
|---|---|---|---|---|---|---|---|
| | 41° C. | | 25° C. | | 4° C. | | −15° C. |
| Hour | A | $\frac{A}{D} \times 100\%$ | B | $\frac{B}{D} \times 100\%$ | C | $\frac{C}{D} \times 100\%$ | D |
| 0.0 | 20.0 | 100 | 20.0 | 100 | 20.0 | 100 | 20.0 |
| 1.0 | 19.0 | 95 | | N/A[1] | | N/A | 20.0 |
| 2.0 | 20.0 | 100 | | N/A | | N/A | 20.0 |
| 3.0 | 20.0 | 100 | | N/A | | N/A | 20.0 |
| 4.0 | 20.0 | 92 | 22.0 | 101 | 21.0 | 96 | 22.0 |
| 5.0 | 12.0 | 55 | | N/A | | N/A | 22.0 |
| 6.0 | 13.0 | 60 | | N/A | | N/A | 22.0 |
| 7.0 | 15.0 | 69 | | N/A | | N/A | 22.0 |
| 8.0 | 16.0 | 74 | | N/A | | N/A | 22.0 |
| 9.0 | 18.0 | 83 | 20.0 | 92 | 22.0 | 101 | 22.0 |
| 10.0 | 6.0 | 42 | | N/A | | N/A | 14.0 |
| 11.0 | <5.0 | N/A | | N/A | | N/A | 14.0 |
| 12.0 | 13.0 | 91 | | N/A | | N/A | 14.0 |
| 15.0 | 5.0 | 50 | 10.0 | 100 | 11.0 | 110 | 10.0 |
| 24.0 | 8.0 | 56 | 15.0 | 104 | 15.0 | 104 | 14.0 |
| 30.0 | 9.0 | 50 | | N/A | | N/A | 18.0 |
| 36.0 | 7.0 | 39 | 17.0 | 94 | 18.0 | 100 | 18.0 |
| 48.0 | <5.0 | N/A | 15.0 | 80 | 17.0 | 91 | 19.0 |
| 56.0 | <5.0 | N/A | 15.0 | 86 | 18.0 | 103 | 17.0 |
| 72.0 | <5.0 | N/A | 18.0 | 93 | 20.0 | 103 | 19.0 |
| 80.0 | <5.0 | N/A | 13.0 | 67 | 19.0 | 98 | 19.0 |

[1]N/A denotes not available.

TABLE XXX

| | | | | LDH @ pH 6.5 in Human Serum Matrix | | | |
|---|---|---|---|---|---|---|---|
| | 41° C. | | 37° C. | | 32° C. | | −15° C. |
| Hour | A | $\frac{A}{D} \times 100\%$ | B | $\frac{B}{D} \times 100\%$ | C | $\frac{C}{D} \times 100\%$ | D |
| 0.0 | 430.0 | 100 | 430.0 | 100 | 430.0 | 100 | 430.0 |
| 4.0 | 420.0 | 98 | 434.0 | 101 | 426.0 | 99 | 430.0 |
| 8.0 | 456.0 | 101 | 449.0 | 100 | 458.0 | 102 | 451.0 |
| 24.0 | 423.0 | 91 | 420.0 | 91 | 442.0 | 95 | 464.0 |
| 48.0 | 461.0 | 103 | 477.0 | 106 | 441.0 | 98 | 449.0 |
| 72.0 | 413.0 | 92 | 429.0 | 95 | 459.0 | 102 | 451.0 |
| 96.0 | 400.0 | 89 | 416.0 | 92 | 437.0 | 97 | 451.0 |
| 121.0 | 417.0 | 88 | 438.0 | 92 | 471.0 | 99 | 474.0 |
| 144.0 | 417.0 | 87 | 432.0 | 90 | 462.0 | 97 | 478.0 |
| 336.0 | 364.0 | 86 | 372.0 | 88 | 414.0 | 98 | 423.0 |
| 504.0 | 352.0 | 84 | 368.0 | 87 | 395.0 | 94 | 421.0 |

TABLE XXXI

| | | | | LDH @ pH 8.5 in Human Serum Matrix | | | |
|---|---|---|---|---|---|---|---|
| | 41° C. | | 37° C. | | 32° C. | | −15° C. |
| Hour | A | $\frac{A}{D} \times 100\%$ | B | $\frac{B}{D} \times 100\%$ | C | $\frac{C}{D} \times 100\%$ | D |
| 0.0 | 488.0 | 100 | 488.0 | 100 | 488.0 | 100 | 488.0 |
| 4.0 | 476.0 | 98 | 487.0 | 100 | 478.0 | 98 | 488.0 |
| 8.0 | 504.0 | 105 | 529.0 | 110 | 531.0 | 110 | 482.0 |
| 24.0 | 438.0 | 89 | | N/A[1] | 476.0 | 97 | 491.0 |
| 48.0 | 436.0 | 88 | 471.0 | 95 | 482.0 | 97 | 498.0 |
| 72.0 | 478.0 | 92 | 505.0 | 97 | 521.0 | 100 | 520.0 |
| 96.0 | 428.0 | 81 | 472.0 | 90 | 504.0 | 96 | 527.0 |
| 172.0 | 405.0 | 78 | 451.0 | 86 | 470.0 | 90 | 522.0 |
| 316.0 | 353.0 | 69 | 404.0 | 79 | 449.0 | 87 | 514.0 |
| 484.0 | 309.0 | 59 | 406.0 | 78 | 484.0 | 93 | 521.0 |
| 1204.0 | 106.0 | 20 | 209.0 | 39 | 425.0 | 80 | 530.0 |

[1]N/A denotes not available.

Table XXXII compares the shelf life for each of the constituents listed in Tables XII–XXXI at a given temperature and time.

TABLE XXXII

| | | | % Recovery | |
|---|---|---|---|---|
| Constituent | pH | Temp.(C°.)/Time(Hr.) | Human Albumin Matrix | Human Serum Matrix |
| ALP | 6.5 | 41/144 | 78% | 55% |
| ALP | 8.5 | 41/96 | 97% | 64% |
| CK | 6.5 | 41/48 | 55% | 53% |
| CK | 8.5 | 41/24 | 13% | 2% |
| SGOT | 6.0 | 41/48 | 92% | 20% |
| SGOT | 8.5 | 41/72 | 98% | 50% |
| SGPT | 6.0 | 41/48 | 87% | 47% |
| SGPT | 8.5 | 41/24 | 79% | 56% |
| LDH | 6.5 | 41/∼505 | 84% | 84% |
| LDH | 8.5 | 41/96 | 87% | 81% |

Table XXXII demonstrates that irrespective of pH enzymes tend to exhibit a markedly improved shelf life when stored in the human serum albumin matrix of the instant invention than when stored in the prior art human serum matrix of the composition of Maurukas I and Maurukas II, supra.

Based on this disclosure, many other modifications and ramifications will naturally suggest themselves to those skilled in the art. These are intended to be comprehended as within the scope of this invention.

The embodiments of the invention in which an exclusive property or privilege is claimed are defined as follows:

1. An enzyme reference composition of the type comprising:
   (a) at least one enzyme constituent of known value;
   (b) from about 20 to about 40 weight percent of at least one alkylene polyol having from 2 to 5 carbon atoms;
   (c) from about 3 to about 8 grams per deciliter total protein; and
   (d) from about 60 to about 80 weight percent water; characterized in that said total protein consists essentially of human serum albumin.

2. The composition of claim 1 having a pH of from about 5.8 to about 8.7.

3. The composition of claim 1 having a pH of from about 6 to about 8.5.

4. The composition of claim 1 having a pH of from about 6 to about 7.

5. The composition of claim 1 having a pH of from about 6.4 to about 6.6.

6. The composition of any one of claims 2–5 or 1 comprising from about 30 to about 34 weight percent of said alkylene polyol, from about 4 to about 5 grams per deciliter of total protein, and from about 66 to about 70 weight percent water.

7. The composition of any one of claims 2–5 or 1 wherein at least one of said enzymes is selected from a group consisting of acid phosatase, aldolase, alkaline phosphatase, amylase, cholinesterase, creatine kinase, α-glytamyl transpeptidase, α-hydroxybutyric dehydrogenase, isocitric dehydrogenase, lactic dehydrogenase, leucine aminopeptidase, lipase, alanine amino transferase, and aspartate amino transferase.

8. The composition of any one of claims 2–5 or 1 wherein said enzyme moiety comprises acid phosphatase, alkaline phosphatase, amylase, creatine kinase, aspartate amino transferase, alanine amino transferase, γ-glutamyl transpeptidase, and lactic dehydrogenase.

9. The composition of any one of claims 2–5 or 1 comprising:
(a) from about 0 to about 350 International Units per liter alkaline phosphatase;
(b) from about 0 to about 20 International Units per liter acid phosphatase;
(c) from about 0 to about 400 International Units per liter amylase;
(d) from about 0 to about 600 International Units per liter creatine kinase;
(e) from about 0 to about 200 International Units per liter aspartate amino transferase;
(f) from about 0 to about 200 International Units per liter alanine amino transferase;
(g) from about 0 to about 300 International Units per liter γ-glutamyl transpeptidase; and
(h) from about 0 to about 500 International Units per liter lactic dehydrogenase wherein the enzyme activities are stated for 37° C.

10. The composition of any one of claims 2–5 or 1 further comprising sodium, potassium, calcium, phosphorous, and magnesium.

11. The composition of any one of claims 2–5 or 1 comprising:
(a) from about 0 to about 350 International Units per liter alkaline phosphatase;
(b) from about 0 to about 20 International Units per liter acid phosphatase;
(c) from about 0 to about 400 International Units per liter amylase;
(d) from about 0 to about 600 International Units per liter creatine kinase;
(e) from about 0 to about 200 International Units per liter aspartate amino transferase;
(f) from about 0 to about 200 International Units per liter alanine amino transferase;
(g) from about 0 to about 300 International Units per liter γ-glytamyl transpeptidase;
(h) from about 0 to about 500 International Units per liter lactic dehydrogenase;
(i) from about 125 to about 157 milliequivalents per liter sodium;
(j) from about 3.5 to about 4.5 millequivalents per liter potassium;
(k) from about 8.4 to about 10.6 milligrams per deciliter calcium;
(l) from about 1.6 to about 2.4 milligrams per deciliter phosphorous;
(m) from about 1.6 to about 2.4 milligrams per deciliter magnesium; and
(n) from about 88 to about 112 milliequivalents per liter chloride;
wherein the enzyme activities are stated for 37° C.

12. The composition of any one of claims 2–5 or 1 comprising:
(a) from about 0 to about 350 International Units per liter alkaline phosphatase;
(b) from about 0 to about 20 International Units per liter acid phosphatase;
(c) from about 0 to about 400 International Units per liter amylase;
(d) from about 0 to about 600 International Units per liter creatine kinase;
(e) from about 0 to about 200 International Units per liter aspartate amino transferase;
(f) from about 0 to about 200 International Units per liter alanine amino transferase;
(g) from about 0 to about 300 International Units per liter γ-glytamyl transpeptidase;
(h) from about 0 to about 500 International Units per liter lactic dehydrogenase;
(i) from about 125 to about 157 milliequivalents per liter sodium;
(j) from about 3.5 to about 4.5 milliequivalents per liter potassium;
(k) from about 8.4 to about 10.6 milligrams per deciliter calcium;
(l) from about 1.6 to about 2.4 milligrams per deciliter phosphorous;
(m) from about 1.6 to about 2.4 milligrams per deciliter magnesium; and
(n) from about 88 to about 112 milliequivalents per liter chloride;
wherein the enzyme activities are stated for 37° C.; and wherein said acid phosphatase is derived from human seminal fluid, said alkaline phosphatase is derived from calf intestine; said amylase is derived from pig pancreas; said creatine kinase is derived from monkey muscle; said aspartate amino transferase and alanine amino transferase are derived from pig heart; said γ-glutamyl transpeptidase is derived from pig intestine; and said lactic dehydrogenase is derived from chicken heart.

* * * * *